United States Patent
Fridberg et al.

(10) Patent No.: US 8,511,651 B2
(45) Date of Patent: Aug. 20, 2013

(54) HEATER UNIT HUMIDIFICATION CHAMBER MONITOR

(75) Inventors: Mikhail Fridberg, Sharon, MA (US); Boris Dubinsky, Newton, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 388 days.

(21) Appl. No.: 13/074,434

(22) Filed: Mar. 29, 2011

(65) Prior Publication Data

US 2012/0248636 A1   Oct. 4, 2012

(51) Int. Cl.
*B01F 3/04*   (2006.01)

(52) U.S. Cl.
USPC ..... 261/142; 261/121.1; 219/442; 219/443.1; 219/446.1; 219/448.11; 219/448.12; 128/203.27; 128/204.17

(58) Field of Classification Search
USPC .............. 261/119.1, 121.1, 142; 219/442, 219/438, 441, 443.1, 451.1, 446.1, 448.11, 219/448.12; 128/203.26, 203.27, 204.17
See application file for complete search history.

(56) References Cited

U.S. PATENT DOCUMENTS

| | | | |
|---|---|---|---|
| 4,038,980 A | 8/1977 | Fodor | |
| 4,051,205 A | 9/1977 | Grant | |
| 4,305,388 A | 12/1981 | Brisson | |
| 4,564,748 A | 1/1986 | Gupton | |
| 4,621,632 A | 11/1986 | Bartels et al. | |
| 4,733,149 A | 3/1988 | Culberson | |
| 4,889,280 A | 12/1989 | Grald et al. | |
| 4,955,372 A | 9/1990 | Blackmer et al. | |
| 5,053,968 A | 10/1991 | Uchinami | |
| 5,341,651 A | 8/1994 | Inoue | |
| 5,365,922 A | 11/1994 | Raemer | |
| 5,368,786 A | 11/1994 | Dinauer et al. | |
| 5,558,084 A | 9/1996 | Daniell et al. | |
| 5,769,071 A | 6/1998 | Turnbull | |
| 5,938,984 A | 8/1999 | Jung | |
| 5,943,473 A | 8/1999 | Levine | |
| 6,078,730 A | 6/2000 | Huddart et al. | |

(Continued)

FOREIGN PATENT DOCUMENTS

| EP | 0845277 B1 | 11/2003 |
|---|---|---|
| EP | 1522299 A2 | 4/2005 |

(Continued)

OTHER PUBLICATIONS

Official Action in related U.S. Appl. No. 11/927,013 dated Feb. 2, 2011 (6 pages).

(Continued)

*Primary Examiner* — Robert A Hopkins
(74) *Attorney, Agent, or Firm* — Wood, Herron & Evans, LLP

(57) ABSTRACT

A heater unit is adapted to determine if a humidification chamber thermally coupled to a hot plate of the heater unit is effectively dry based on determining a thermal response of a hot plate of the heater unit. Also, the activation period during which the hot plate is being heated is adjusted toward an optimum period by adjusting the energization or power level to the heater element thereof in relation to the duration of a prior activation period. Further, the air flow rate of gas through the humidification chamber may be estimated based on a temperature of the hot plate determined in predetermined relationship to the beginning of an activation period.

43 Claims, 4 Drawing Sheets

(56) References Cited

U.S. PATENT DOCUMENTS

| | | | |
|---|---|---|---|
| 6,082,714 | A | 7/2000 | Dornfest et al. |
| 6,095,505 | A * | 8/2000 | Miller .......................... 261/130 |
| 6,258,170 | B1 | 7/2001 | Somekh et al. |
| 6,272,933 | B1 | 8/2001 | Gradon et al. |
| 6,349,722 | B1 | 2/2002 | Gradon et al. |
| 6,455,820 | B2 | 9/2002 | Bradenbaugh |
| 6,471,781 | B1 | 10/2002 | Tobe et al. |
| 6,584,972 | B2 | 7/2003 | McPhee |
| 6,590,366 | B1 | 7/2003 | Browning et al. |
| 6,653,605 | B2 | 11/2003 | Kneuer |
| 6,694,974 | B1 | 2/2004 | George-Gradon et al. |
| 6,698,186 | B2 | 3/2004 | Ueno et al. |
| 6,711,891 | B2 | 3/2004 | Kitamura et al. |
| 6,739,337 | B2 | 5/2004 | Isaza |
| 6,802,314 | B2 | 10/2004 | McPhee |
| 6,813,895 | B2 | 11/2004 | Eisenhower et al. |
| 6,895,803 | B2 | 5/2005 | Seakins et al. |
| 6,918,389 | B2 | 7/2005 | Seakins et al. |
| 6,920,388 | B2 | 7/2005 | Yasui |
| 6,966,364 | B1 | 11/2005 | Babikian et al. |
| 6,988,497 | B2 | 1/2006 | Levine |
| 7,051,733 | B2 | 5/2006 | Gradon et al. |
| 7,086,399 | B2 | 8/2006 | Makinson et al. |
| 7,106,955 | B2 | 9/2006 | Thudor et al. |
| 7,140,367 | B2 | 11/2006 | White et al. |
| 7,146,979 | B2 | 12/2006 | Seakins et al. |
| 7,306,205 | B2 | 12/2007 | Huddart et al. |
| RE40,806 | E | 6/2009 | Gradon et al. |
| 7,681,571 | B2 | 3/2010 | Makinson et al. |
| 7,722,016 | B2 | 5/2010 | Bradley et al. |
| 2002/0112725 | A1 | 8/2002 | Thudor et al. |
| 2002/0129815 | A1 | 9/2002 | McPhee |
| 2002/0139367 | A1 | 10/2002 | McPhee |
| 2002/0144681 | A1 | 10/2002 | Cewers et al. |
| 2003/0154977 | A1 | 8/2003 | White et al. |
| 2003/0201684 | A1 | 10/2003 | Browning et al. |
| 2003/0209246 | A1 | 11/2003 | Schroeder et al. |
| 2004/0060558 | A1 | 4/2004 | Gradon et al. |
| 2004/0074493 | A1 | 4/2004 | Seakins et al. |
| 2004/0079370 | A1 | 4/2004 | Gradon et al. |
| 2004/0102731 | A1 | 5/2004 | Blackhurst et al. |
| 2004/0149284 | A1 | 8/2004 | Smith et al. |
| 2004/0221844 | A1 | 11/2004 | Hunt et al. |
| 2006/0201506 | A1 | 9/2006 | Makinson et al. |
| 2008/0028850 | A1 | 2/2008 | Payton et al. |
| 2008/0054497 | A1 | 3/2008 | Bradley et al. |
| 2008/0054500 | A1 | 3/2008 | Bradley et al. |
| 2008/0142019 | A1 | 6/2008 | Lewis et al. |
| 2008/0190427 | A1 | 8/2008 | Payton et al. |
| 2008/0310994 | A1 | 12/2008 | O'Donnell et al. |
| 2009/0065002 | A1 | 3/2009 | Hunt et al. |
| 2009/0107980 | A1 | 4/2009 | Andel et al. |
| 2009/0110379 | A1 | 4/2009 | McGhin et al. |
| 2010/0242963 | A1 | 9/2010 | Brieger et al. |

FOREIGN PATENT DOCUMENTS

| | | |
|---|---|---|
| EP | 1514570 B1 | 8/2011 |
| EP | 2098260 B1 | 4/2012 |
| WO | 0113981 A1 | 3/2001 |
| WO | 03030790 A1 | 4/2003 |
| WO | 2009064202 A2 | 5/2009 |
| WO | 2009145646 A1 | 12/2009 |

OTHER PUBLICATIONS

Official Action in related U.S. Appl. No. 11/927,013 dated Apr. 12, 2011 (6 pages).

European Search Report in related European Application No. 08167307.1-2350 dated Jan. 30, 2009 (5 pages).

Manual for Fisher & Paykel Model Nos. MR700, MR720, MR730 Respiratory Humidifiers (Mar. 1998) (48 pages).

Technical Manual for Fisher & Paykel Respiratory Humidifier Model Nos. MR700, MR720, MR730, MR480 (Mar. 2001) (64 pages).

Allegiance Healthcare 510K No. K993833 for Airlife® Heated Ventilator and Anesthesia Breathing Circuits (Dec. 10, 1999) (5 pages).

Brochure for Hudson RCI Humid-Heat® (6 pages).

Operating Manual for Fisher & Paykel Model Nos. MR700, MR720, MR730 Respiratory Humidifiers (Mar. 1994) (46 pages).

Instruction Sheet for Airlife® Single Heated Adult Respiratory Circuit (date uncertain) (2 pages).

Cardinal Health RT110 Data for Circuits, reprinted from the Internet Jun. 3, 2006 (2 pages).

Fisher & Paykel 900MR561 Probe Label (date uncertain) (1 page).

Fisher & Paykel Airway Temperature Probes Instructions for Use (2003) (3 pages).

Cat. RT110 Insert for AirlifeTM Adult Respiratory Circuit—Heated (undated) (1 page).

Partial International Search Report issued, with Invitation to pay Additional Fees, in counterpart PCT Application No. PCT/US2012/024055, mailed on Jun. 13, 2012 (4 pages).

International Search Report and Written Opinion issued in counterpart PCT Application No. PCT/US2012/024055, mailed on Oct. 10, 2012 (16 paages).

* cited by examiner

HEATER UNIT HUMIDIFICATION CHAMBER MONITOR

FIELD OF THE INVENTION

The present invention relates to heater units adapted to monitor humidification chambers coupled thereto and used to heat and humidify gases, such as breathable gases in a respiratory system.

BACKGROUND OF THE INVENTION

Respiratory systems provide breathable gas, such as oxygen, anesthetic gas, and/or air directly to a patient's mouth, nose, or airway to assist or facilitate breathing by the patient. A ventilator may be used as part of the respiratory system to drive the breathable gas to the patient through an inspiratory limb hose or conduit of a breathing circuit. The breathing circuit may include an expiratory limb hose or conduit to carry expelled air and other gas(es) from the patient back to the ventilator.

It is typically desired to warm and impart humidity to the breathable gas before it is provided to the patient. For that purpose, many respiratory systems include a humidification system having a humidification chamber for holding water and a heater unit to which the humidification chamber may be releasably mounted. The humidification chamber is typically a dome-shaped plastic member with a thermally conductive metal base plate, and is typically intended to be disposable so as not to be reused from patient to patient. The heater unit includes a heater, which may be comprised of one or more heater elements and a metal plate defining a hot plate. A wall of the humidification chamber, such as the thermally conductive metal base plate, is placed into thermal contact with the hot plate of the heater, to thus heat the water in the humidification chamber. The breathable gas is coupled into and passed through the humidification chamber to be heated and humidified before being passed on to the patient, such as through the inspiratory limb of the breathing circuit. Examples of heater unit and humidification chambers are shown in U.S. Pat. Nos. 6,988,497 and 5,943,473, the disclosures of both of which are incorporated herein by reference as if fully set forth herein.

Typical heater units may also include a processor-based control responsive to one or more temperatures of the system by which to control the heater, as well as heater elements which may be associated the inspiratory and/or expiratory limbs of the breathing circuit. For example, a sensor such as a thermocouple thermally coupled to the hot plate indicates to the control the current temperature of the hot plate. By way of example, the gas temperature is monitored either at the humidification chamber outlet or at the patient. In a typical thermostatic controlled system, the hot plate heater element is energized with a fixed power level when the monitored gas temperature drops to or below a low temperature threshold so as to heat up the hot plate. The water, in turn, heats up which imparts heat and humidity to the gas passing through the humidification chamber. The heater element is then turned off when the gas temperature increases to a high temperature threshold, and the hot plate begins to cool. The water and thus the gas temperature will in turn begin to cool until the gas temperature decreases again to the low temperature threshold at which the heater element is again energized. The period of time during which the heater element is energized may be referred to herein as an "activation period" whereas the time during which the heater element is not being energized may be referred to herein as a "cooling period." Together, an activation period and a cooling period may be seen as making up a heating cycle.

Similarly, the gas temperature to the patient can be indicated by sensors associated with the inspiratory limb adjacent the humidification chamber or adjacent the patient. One or more of those temperatures can be utilized by the processor(s) to selectively energize the hot plate heater elements and/or limb heater elements with the goal of attaining a desired temperature set point of the humidified, breathable gas. Moreover, should any of the temperatures being monitored exceed an applicable maximum level or differential, the heater unit may be shut down and/or caused to set off an alarm. An example of a processor-based control is shown in U.S. Patent Publication No. 2009/0110379, the disclosure of which is incorporated herein by reference as if fully set forth herein.

As the breathable gas passes through the humidification chamber, the water therein is depleted such as by evaporation. The humidification chamber may be manually refillable, or there may be a water source to selectively fill the humidification chamber as it empties. However, situations might arise where the water level in the humidification chamber becomes so low that the humidification chamber is effectively dry. As a consequence, the breathable gas passing through the humidification chamber exits into the breathing circuit with insufficient humidity. Current heater units are not equipped to monitor the water level in the humidification chamber, leaving it to the caregivers to devote significant time and effort to manually monitor the humidification chamber and determine if there is an acceptable level of water present. While it may be possible to automatically monitor the level with a sensor associated with the humidification chamber, that approach is not desirable. Not only is there the added cost of the sensor(s) for doing so, but the processor-based control of the heater unit would have to be adapted to communicate with an additional sensor, thus adding cost and complexity to the heater unit.

SUMMARY OF THE INVENTION

In one aspect, the present invention provides a method and apparatus for automatically monitoring the water level in the humidification chamber without the need for manual monitoring or additional sensors or the like. To that end, and in accordance with the principles of that one aspect of the present invention, a determination of whether the humidification chamber is effectively dry is accomplished by evaluating the thermal response of the hot plate based on monitoring the temperature of the hot plate over a period of time (which may be referred to as a "sampling period"), such as over all or part of an activation period (although the period of time could instead be over all or part of a cooling period). The hot plate temperature may be monitored with a sensor already provided for that purpose and electrically coupled to the control, such that an additional sensor is not necessary. Instead, the processor-based control is adapted to utilize the monitored hot plate temperature over the sampling period to determine the thermal response and determine therefrom whether the humidification chamber is effectively dry.

More particularly, we have determined that the thermal response of the hot plate when the humidification chamber is effectively dry defines a curve that, if plotted, essentially approaches a straight line temperature response over the sampling period, whereas the thermal response when the humidification chamber has sufficient water results in a rate of change of the temperature that varies over time to produce a curve which, if plotted, has a substantial degree of arc as a temperature response over that same sampling period. To that end, and in accordance with this one aspect of the present invention, the temperature of the hot plate may be advantageously sampled over a period of time, such as during the activation period while heat is being applied thereto or during the cooling period while heat is not being applied thereto, to measure the thermal response of the hot plate. After a number of samples have been obtained, the processor, in effect, determines the shape of the temperature response from the temperature samples taken during the sampling period to determine if the degree of the curve is sufficiently close to a straight line curve to indicate that the humidification chamber is effectively dry, or if the degree of the curve sufficiently departs from a straight line curve, such as by being sufficiently arced, that there is expected to be sufficient fluid in the humidification chamber, in which event the humidification chamber is not considered effectively dry.

While a number of "curve fit" methodologies may be employed to make the determination, one advantageous methodology involves the processor accumulating the differences between the sampled temperatures and a starting temperature over the sampling period to generate a thermal response value, and generating a base-line value correlated to the difference between the starting temperature and the last-sampled temperature, the latter being representative of the expected thermal response value of an effectively dry humidification chamber. The processor compares the thermal response value to the base-line value to make a determination whether the humidification chamber is effectively dry, the determination being affirmative if, for example, the thermal response value is sufficiently close to the base-line value.

To that end, the determination can be made by comparing the ratio of the thermal response value to the base-line value against a threshold value. For example, if the ratio is greater than the threshold value, the thermal response is deemed sufficiently arced that the humidification chamber will be considered to have sufficient water. In that event, the determination is not made that the humidification chamber is effectively dry (which, for purposes of the present invention is considered the same as making a determination that the humidification chamber has an acceptable level of water therein). By contrast, if the ratio is below the threshold value, the thermal response is sufficiently close to a straight line that the humidification chamber will be determined to be effectively dry. If the ratio is at the threshold value, the determination may be made that the humidification chamber is effectively dry or is considered to have sufficient water to avoid such a determination, depending on the chosen threshold. The temperature readings from the hot plate sensor over time can thus be accumulated by the processor in order to determine the thermal response. Based thereon, the processor can automatically determine if the humidification chamber is effectively dry, and if so, an alarm may be generated to alert the caregiver.

By virtue of the foregoing, in accordance with one aspect of the present invention, there is thus provided a method and apparatus for automatically monitoring the water level in the humidification chamber without the need for manual monitoring, or additional sensors or the like.

While the low and high temperature thresholds are selected to cause the heater unit to attempt to achieve a desired set point of the heated and humidified gas, the activation period is not fixed but varies due to operational parameters over which the heater unit has no control, such as air flow rate of the gas through the humidification chamber and/or the thermal mass of the water in the humidification chamber. We have determined, however, that the sampling period should not be so short that even with sufficient water the effective "curve" will be sufficiently close to a straight line as to cause the processor to determine that the humidification chamber is effectively dry. Similarly, we have determined that the sampling period should not be so long that even when effectively dry, the temperature samples will result in an arced "curve" indicative of sufficient water in the humidification chamber such that the processor will not determine that the humidification chamber is effectively dry. In one embodiment, we have determined that the sampling period should be about one minute, with temperature samples taken every second, such as starting no earlier than when, or shortly after (such as about seven seconds after), the activation period begins and during the activation period such that the sampling period ends no later than when, and advantageously somewhat before, the activation period ends. In that regard, it is advantageous to be sure the activation period will not stop before the end of the sampling period. And while the activation period can also be substantially longer than the sampling period, we have determined that if the activation period gets overly long, the heat input from the hot plate may be insufficient to completely heat the gas passing through the humidification chamber, and may also affect the ability of the processor to detect if the humidification chamber is effectively dry.

To that end, and in accordance with the principles of a second aspect of the invention, an optimum activation period of the hot plate heater cycle is selected and the processor is adapted to adjust the power level to the hot plate heater element during an activation period so as to increase or decrease the amount of time necessary to raise the gas temperature from the low temperature threshold to the high temperature threshold based on the duration of a prior activation period. The activation period may thus vary from heating cycle to heating cycle in an effort to achieve an activation period that is at or sufficiently close to the optimum activation period to provide a thermal response and base-line value that can be relied upon to make the determination whether the humidification chamber is effectively dry.

By way of example, an optimum activation period is selected at eighty five seconds. With each heating cycle, the processor determines how long it takes to raise the temperature of the gas from the low temperature threshold to the high temperature threshold, which defines an activation period. If the duration of that activation period exceeds eighty five seconds, the power level applied to the heater during the activation period of a subsequent heating cycle, such as the next heating cycle, will be increased in an effort to reduce the time necessary to reach the high temperature threshold and thus drive the activation period down toward the optimum activation period. If, however, the duration of the activation period is less than eighty five seconds, the power level applied to the heater for the subsequent heater cycle will be reduced in an effort to increase the time necessary to reach the optimum activation period. In either case, the processor adjusts the power, such as by varying the duty cycle of a triac used to switch the heater element on and off, by an amount proportional to the difference between the prior activation period and the optimal activation period, so that larger discrepancies result in larger power adjustments for the subsequent activation period.

In one embodiment, a first activation period may begin with a predetermined power level applied to the heater, such as 75 watts. As the activation period is monitored and determined to depart from the optimum activation period, the power level for a subsequent activation period is adjusted up or down in proportion or other relationship to the difference from the optimum activation period.

In some situations, the higher temperature threshold may not be attained until long after the desired optimum activation period. In such situations, if the duration of an activation period extends beyond some multiple of the optimum activation period, such as 2.0 times the optimum activation period, the processor will automatically cause the power level to the hot plate heater element to be increased by a fixed amount, such as 25 watts, and a new activation period begun (along with making the determination whether the humidification chamber is effectively dry as previously discussed). The power may be incremented again each time if the duration of the activation period continues to exceed the multiple of the optimum activation period until the maximum power level available is being supplied to the heater element. If, at that maximum power level, the duration of the activation period still exceeds the multiple, then the heater will be turned off to allow the hot plate to cool (until the hot plate temperature drops by 8° C. but not more than 20 seconds, by way of example). The heater element is then turned on at full power, and the temperatures again taken over a sampling period to, again, determine whether the humidification chamber is effectively dry.

If the maximum power level is being used, then turning off the heater element for cooling using the same multiple of the optimum activation period might lead to less than complete heating of the gas passing through the humidification chamber. Such situations might occur if the air flow rate through the humidification chamber is very high, for example. Once at the maximum power level, the time before the heater element is to be turned off for cooling may be increased for subsequent activation periods, such as by 5%. The increases may be capped at a maximum, such as 160 seconds. However, once the duration of an activation period falls below the optimum activation period, the power level will be decreased in order to increase a subsequent activation period.

By virtue of the foregoing, there is thus provided by the second aspect of the present invention, a method by which the heater element activation period in a heating cycle of the hot plate may be maintained at, or sufficiently close to, a generally optimum time period that the ability to determine if the humidification chamber is effectively dry is not compromised.

In some situations, it may be helpful to know the air flow rate of the gas through the humidification chamber such as for control or notification purposes. However, the ventilator settings are unknown to the heater unit. The heater unit also typically lacks any facility or structure to adjust or control the air speed or pressure through the humidification chamber. A separate sensor could be provided to determine air flow rate, but that is undesirable. We have made the surprising discovery that it is possible to approximate the actual air flow rate from the temperature of the hot plate determined in predetermined relationship to the beginning of an activation period. In that regard, we have determined that the temperature of the hot plate, particularly during a cooling period between activation periods, correlates to the flow rate of the gas through the humidification chamber.

More particularly, the higher the temperature at a particular point in the cooling period, the higher the flow rate. Conversely, the lower the temperature at that particular point, the lower the flow rate. To that end, and in accordance with a third aspect of the present invention, the processor is adapted to determine, at least approximately, the air flow rate based on the temperature of the hot plate taken between activation periods, and advantageously, based on the last temperature sample taken before a new activation period begins. In one embodiment, to conserve processor computational resources, a look-up table is provided in the memory of the heater unit which correlates the temperature reading with a flow rate based, for example, on empirical evidence developed for heater units having a particular hot plate and full humidification chamber configuration (such as would apply to all models of a particular heater unit and related, disposable humidification chambers). Alternatively, for a given hot plate and humidification chamber configuration, it is determined that there is a relationship, such as linear or proportional, between flow rate and sample temperature, such that the processor may be programmed to compute at least an approximation of the actual flow rate based thereon. While the foregoing may be advantageously adjusted based on the gas temperature set point, we have determined that for heater units used with human patients, a sufficiently accurate indication of air flow rate is obtained based on assuming that the set point is standard human body temperature, i.e., 98.6° F. or 37° C.

By virtue of the foregoing, there is thus provided with the third aspect of the present invention, a simple and straightforward method and apparatus implemented in a heater unit for estimating air flow rate of gas through a humidification chamber thermally coupled to the heater unit.

The foregoing and other advantages and features of the invention will be apparent in light of the accompanying drawings and detailed description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF DRAWINGS

Figure 1:
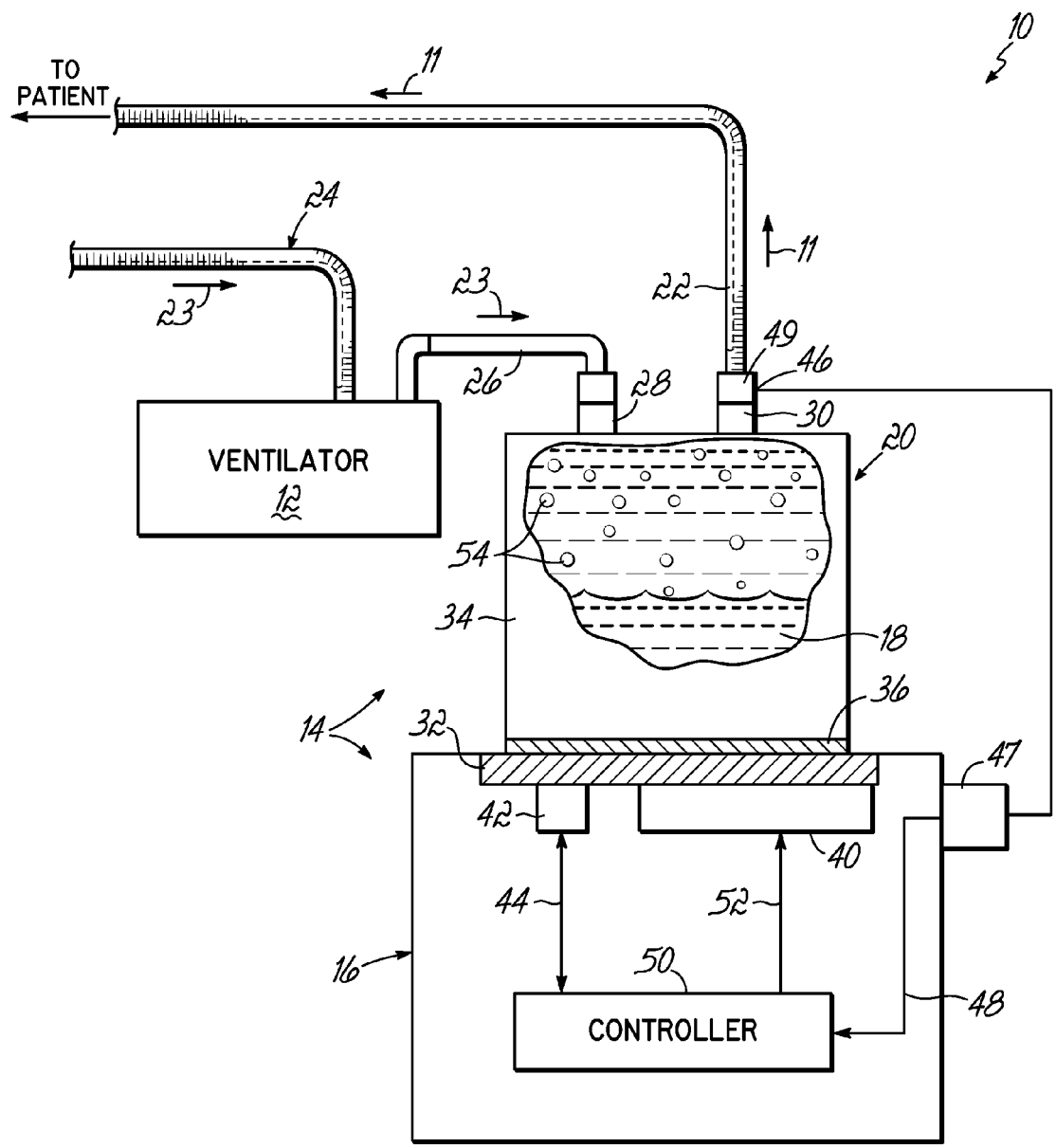
FIG. 1 is a diagram of a respiratory humidifying system embodying principles of the present invention.

FIG. 1 illustrates an exemplary respiratory system 10 for supplying a heated and humidified breathable gas as indicated by arrows 11 to a patient (not shown). The respiratory system 10 includes a ventilator 12, a heating and humidifying system 14 having a heater unit 16 and a heatable container for water 18 such as a disposable humidification chamber 20, and at least an inspiratory breathing circuit limb 22. The ventilator 12 drives breathable gas (as indicated by arrows 23), such as oxygen, anesthetic gas and/or air, from a first gas supply conduit 24, which may be an expiratory limb of a breathing circuit or coupled to a source of fresh gas (not shown), and expels it out through a gas conduit 26 and into humidification chamber 20 such as at an air inlet 28 of the humidification chamber 20. Water 18 is received in the humidification chamber 20, either by being poured in manually or automatically from a water supply (not shown) such as a bag or bottle, and in the latter event, a float control system (also not shown) may be included within the humidification chamber 20 to regulate filling thereof. Heat and humidity are imparted to the gas 23 as it passes through the humidification chamber 20 so that it is expelled as heated and humidified, or conditioned, gas 11 to the patient from the air outlet 30 of the humidification chamber 20 via the limb 22.

The heater unit 16 is adapted to removably receive the humidification chamber 20. To that end, the heater unit 16 includes a hot plate 32 made of a thermally conductive material, such as aluminum, aluminum coated with nickel, steel or any other suitable conductive material. Similarly, the humidification chamber 20 has a main dome-shaped body 34 of plastic, and a bottom plate 36 also of thermally conductive material. The humidification chamber 20 may be as shown in U.S. Pat. No. 7,722,016, the disclosure of which is incorporated herein by reference as if fully set forth herein. The humidification chamber 20 is mounted to the heater unit 16 with their respective plates 32 and 36 in confronting and contacting relationship so as to thermally couple the respective plates 32 and 36 such that heat applied to the hot plate 32 is coupled into the water 18 within the humidification chamber 20 via the bottom plate 36. To provide the heat to the hot plate 32, the heater unit 16 also includes a heater element 40 (which while shown as one such element, may actually comprise a plurality of such elements) in thermal communication with the hot plate 32. A temperature sensor 42, such as a thermocouple or the like, is also in thermal communication with the hot plate 32 to provide plate temperature signals 44 corresponding to the temperature of the hot plate 32. An example of a suitable configuration of the hot plate 32 and the related heater element(s) 40 and thermocouple 42 is shown in U.S. Patent Publication No. 2009/0107980, the disclosure of which is also incorporated herein by reference as if fully set forth herein. A temperature sensor in the form of a probe 46 provides, via connector 47, gas temperature signals 48. The probe 46 may be coupled to the inspiratory limb 22 at the connector 49 thereof coupled to the air outlet 30 of the humidification chamber 20 as shown in FIG. 1, or may be coupled to a remote end (not shown) of the limb 22, so as to provide an indication of the temperature of the conditioned gas 11 either at the humidification chamber 20 or at the patient, respectively.

The heater unit 16 also includes a controller 50 which receives the plate temperature signals 44 and the gas temperature signals 48, and utilizes those signals to provide power signals 52 by which to selectively energize the heater element 40 to thereby heat up the water 18 in the humidification chamber 20. The controller 50, or another controller or processor (not shown), may also provide signals (not shown) by which to selectively energize heater elements (not shown) associated with the inspiratory limb 22 and/or expiratory limb (such as the conduit 24). In any event, energization of the heater element 40 causes the water 18 to heat up and/or to form water vapor 54 within the humidification chamber 20. The gas 23 passing through the humidification chamber 20 becomes heated and humidified thereby before going on as conditioned gas 11 to the patient.

Figure 2:
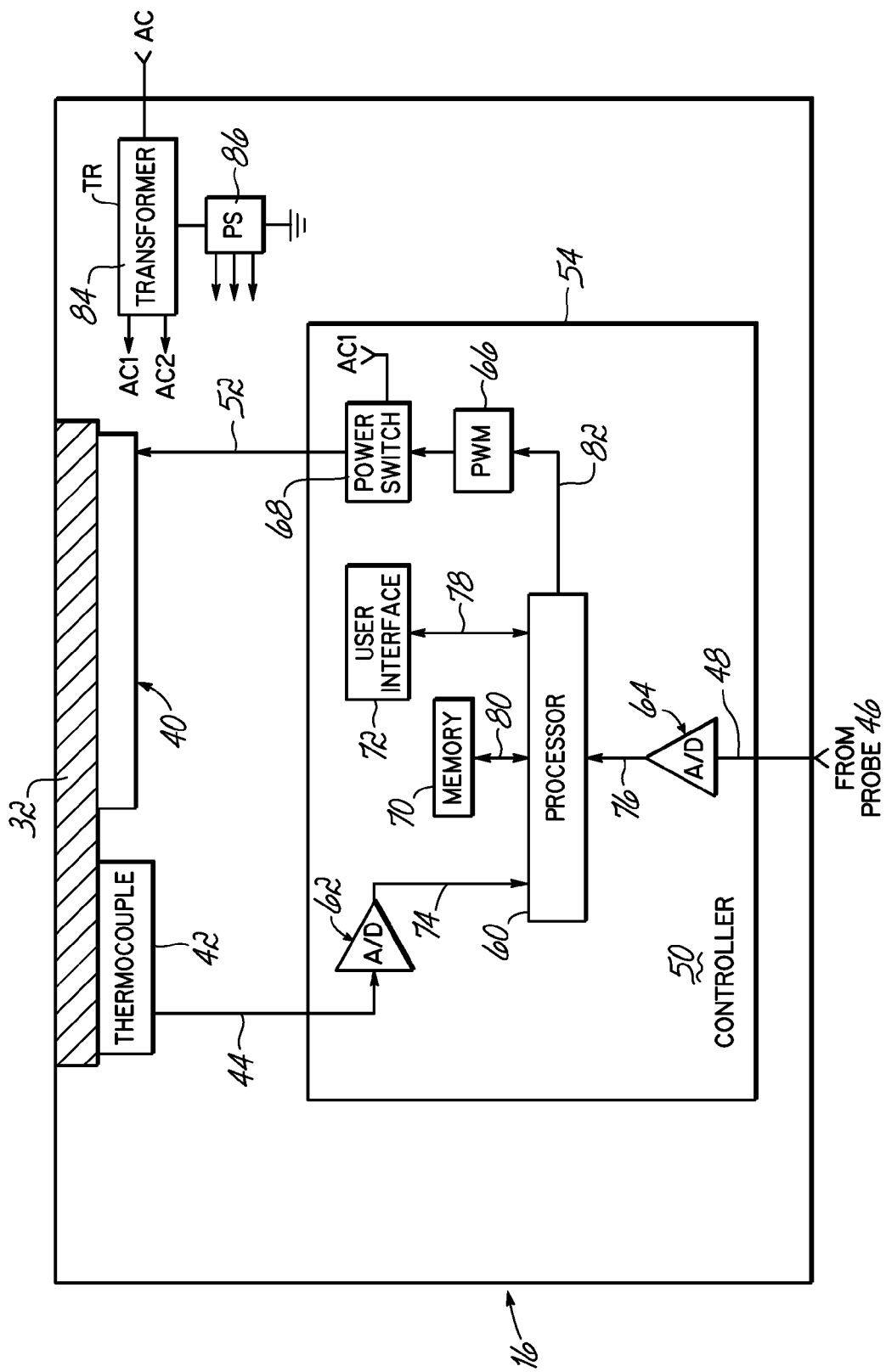
FIG. 2 is a schematic diagram of the heater unit of FIG. 1.

As seen in greater detail in FIG. 2, the controller 50 includes a processor 60, which may be a microcontroller, a microprocessor, or other computer or programmable logic device; at least first and second analog to digital (A/D) converters 62, 64; a power control circuit such as a pulse width modulator or PWM 66; a power switch 68, such as a triac or the like; a memory 70, which may include memory integrated with the processor 60; and a user interface 72. The plate temperature signals 44 from the thermocouple 42 may be voltage signals proportional to the temperature of the hot plate 32 which are converted into a digitally readable form by the first A/D converter 62 and coupled via signal path 74 to the processor 60. In a similar manner, the gas temperature signals 48 from the probe 46 may be voltage signals proportional to the temperature of the out-flowing stream of the breathable gas as it exits the humidification chamber 20. Those voltage signals 48 are converted into a digitally readable form by the second A/D converter 64 and coupled to the processor 60 such as over signal path 76. Although shown as discrete A/D converters 62, 64, the respective functions thereof may alternatively be integrated into the processor 60, in which case the voltage signals 44 and 48 produced by the thermocouple 42 and the probe 46, respectively, may be fed directly to the processor 60.

The user interface 72 may include a keypad, buttons, a dial, or other method for entering data, such as a temperature set point at which the breathable, conditioned gas 11 is desired to be delivered to the patient. The user interface 72 may also include one or more displays to inform the operator of the operational status of the heater unit 16, such as current temperature set point, breathable gas temperature, or any other operational parameter. The user interface 72 communicates with the processor 60 over signal path 78. The memory 70 may store operating programs or algorithms and control data used by the processor 60, as well as input data from the user interface 72, such as the temperature set point. The memory 70 communicates with the processor 60 over signal path 80. As will be readily appreciated, while the signal paths 74, 76, 78, and 80 are shown as being separate from each other, one or more of them may be part of a common communication bus as is typical of microprocessor-based devices.

The processor 60 utilizes the information from the memory 70 and/or the user interface 72, along with the temperature signals 44 and 48 in order to control heating of the hot plate 32. To that end, the processor 60 outputs a power signal 82 to the PWM 66 which, in response thereto, selectively activates the power switch 68 in order to couple power to the heater element 40 so as to raise the temperature of the hot plate 32. The power signal 82 may be varied as will be described such that the duty cycle, i.e., the duration of the on time relative to the off time, of the switch 68 will vary to thus increase or decrease the power or energization level to the heater element 40. In the embodiment of the heater unit 16 shown, when the switch 68 is closed, the heater element 40 is coupled to a suitable power supply voltage, such as an alternating current (AC) voltage from a transformer 84 connected to AC line voltage. When it is desired not to heat up the hot plate 32, the switch 68 is left open (or the duty cycle is caused to be so low from the PWM 66 that, even though the heater element 40 is being minimally energized, it is at a level insufficient to effectively heat up the hot plate 32) such that the hot plate 32 will begin to cool down. The transformer 84 may also provide power to a power supply 86, which may in turn provide one or more regulated direct current (DC) voltage levels for use in powering various components of the system 14, including the controller 50. Other taps (not shown) from the transformer 84 may be used to provide AC voltage for heater elements, if present, in the limbs 22 and/or 24.

The memory 70 of the controller 50 may contain the operating program for the processor 60 by which to regulate the temperature of the hot plate 32. By way of example, a user of the system 10, such as a caregiver or medical provider, enters a desired temperature set point for the conditioned gas 11 via the user interface 72. The temperature set point may be stored in the memory 70 and utilized by the processor 60 to selectively cause the heater element 40 to be turned on or off. The controller 60 may determine a low temperature threshold and a high temperature threshold based on the temperature set point. For example, the high temperature threshold may be 0.1° C. above the temperature set point, and the low temperature threshold may be 0.1° C. below the temperature set point, giving the temperature control system a hysteresis of 0.2° C., although other thresholds may be used as will be readily appreciated. In any event, the gas temperature signals 48 are monitored, such as by being sampled every second, by the processor 60. The sampled gas temperature data is utilized to turn on or energize the heater element 40 when the temperature of the breathable gas drops to (or possibly below as compared to the last sample) the low temperature threshold and to turn off (or de-energize) the heater element 40 when the temperature of the breathable gas reaches (or possibly exceeds as compared to the last sample) the high temperature threshold. The duration from the turn-on to the turn-off defines an activation period, whereas the duration from the turn-off to the next turn-on defines a cooling period.

As the system 10 is being utilized, the humidity imparted to the breathable gas 23 passing through the humidification chamber 20 will tend to reduce the level of the water 18 in the humidification chamber 20. Depending on the supply of the water 18 and other factors, it is possible that the level of the water 18 in the humidification chamber 20 may become so low as to result in the humidification chamber 20 being considered effectively dry such that it is no longer considered possible to impart sufficient humidity to the breathable gas 23 supplied as conditioned gas 11 to the patient (not shown). To that end, and in accordance with the principles of a first aspect of the present invention, a determination of whether the humidification chamber 20 is effectively dry is accomplished by evaluating the thermal response of the hot plate 32 based on monitoring the plate temperature signals 44 over a period of time, such as a sampling period, including all or part of an activation period, so that the determination can be made automatically by the heater unit 16 without the need for manual monitoring or additional sensors or the like.

Figure 3:
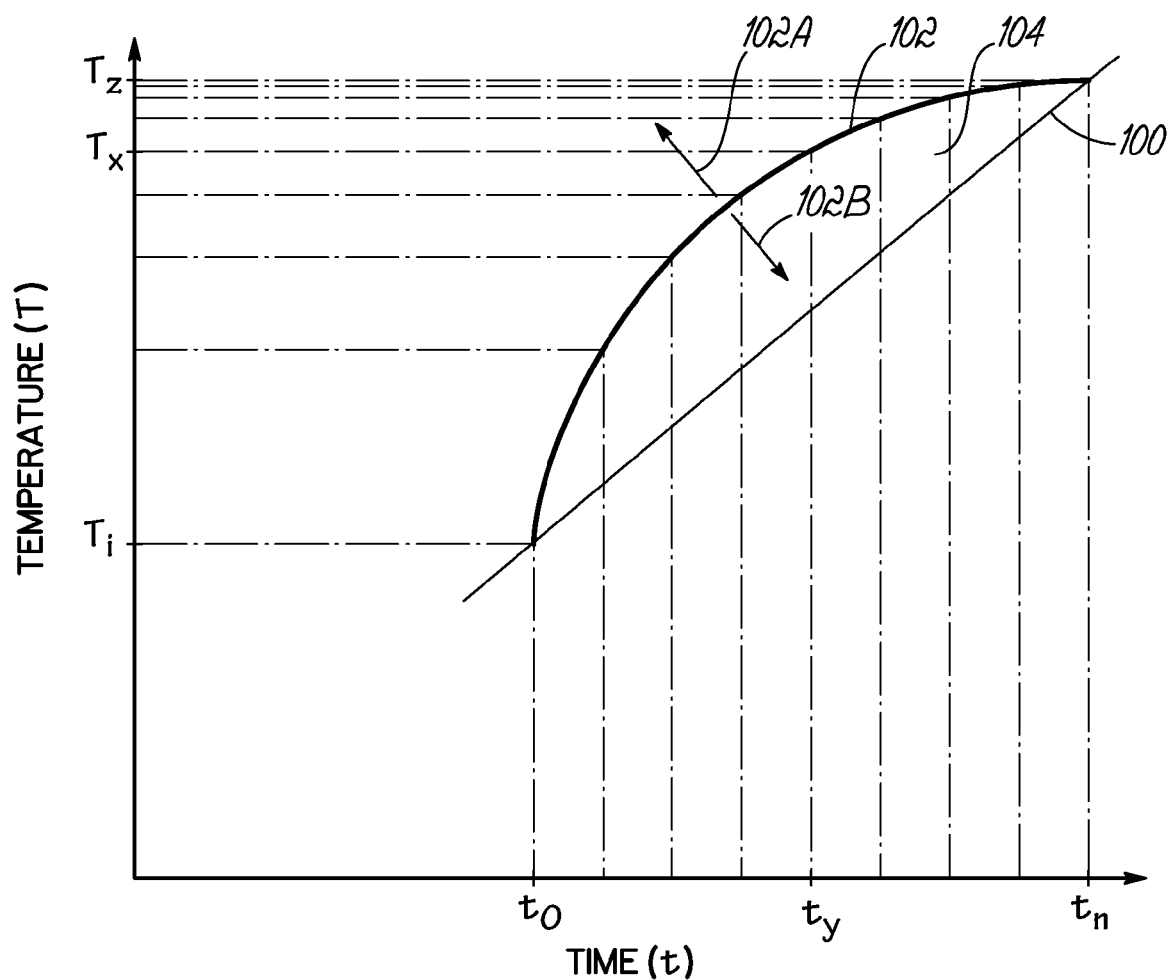
FIG. 3 is a diagram showing various exemplary temperature samples and curves related to operation of the heater unit of FIG. 1 for purposes of explaining the principles of a first aspect of the present invention.

In particular, and with reference to FIG. 3, the thermal response of the hot plate 32 is determined based on samples taken over a sampling period starting at time $t_0$ and ending at time $t_n$. The starting time $t_0$ may be coincident with or shortly after the start of, an activation period, i.e., not earlier than when the gas temperature has decreased to about the low temperature threshold. And the ending time $t_n$ may be coincident with or somewhat before the end of the activation period, i.e., not later than when the gas temperature has increased to about the high temperature threshold. The thermal response will differ depending upon whether there is a sufficient level of the water 18 in the humidification chamber 20 or if the humidification chamber 20 is effectively dry. In one embodiment, the optimum duration of an activation period is advantageously about 85 seconds, and the sampling period is about sixty seconds starting about seven seconds after the activation period begins and ending about 18 seconds before the end of the activation period.

More specifically, if the humidification chamber 20 is effectively dry, the thermal response over the sampling period would be expected to define a curve that approaches or is, if plotted, a straight line between an initial temperature sample $T_i$ taken at or around time $t_0$, and a final temperature sample $T_z$ taken at or around time $t_n$, as exemplified by the curve 100 of FIG. 3. In other words, the degree of the curve is minimal. However, with levels of the water 18 in the humidification chamber 20 above a level at which the humidification chamber 20 would be considered effectively dry, the thermal response will vary over time such as by defining an arc as exemplified by the curve 102 in FIG. 3. The curve 102 will move away or "arc out" from curve 100 when the level of the water 18 is above a level that would be considered effectively dry as exemplified by arrow 102A so as to increase the area 104 between curves 100 and 102 and present a substantial degree of curve. The degree of the curve will quickly decrease, that is the arc of curve 102 will quickly move toward, or tend to flatten out to match, curve 100 as the level of the water 18 approaches or reaches a level that would be considered effectively dry as exemplified by arrow 102B thereby decreasing the area 104. Thus, except where the humidification chamber 20 is effectively dry, the thermal response will define a curve that is arced such as curve 102, whereas when the humidification chamber 20 is effectively dry, the thermal response will define a curve that is closer to a straight line such as curve 100.

In accordance with the principles of this first aspect of the invention, a temperature sample $T_x$ is taken periodically, such as every second (as at $t_y$) over the sampling period to determine the thermal response of the hot plate 32. The thermal response defines a curve and the processor 60 is adapted to evaluate the curve in order to perform a curve fitting algorithm thereto to assess whether the degree of the curve is high enough to be consider closer to an arced curve such as curve 102 or is so low that it is considered closer to a straight line curve such as curve 100. If the processor 60 determines from the curve fitting algorithm that the thermal response is sufficiently close to a straight line curve, a determination is made that the humidification chamber 20 is effectively dry. Similarly, or alternatively, if the processor 60 determines from the curve fitting algorithm that the thermal response is sufficiently close to an arced curve, a determination is not made that the humidification chamber 20 is effectively dry (or a determination being made that the humidification chamber 20 has a sufficient level of water 18 which, for purposes of the present invention, is the same thing as not making a determination that the humidification chamber 20 is effectively dry).

A number of known "curve fit" methodologies may be employed to make the determination. By way of example, an exponential curvefit may be conducted and the resulting coefficients examined to measure a normalized slope of response (which correlates to the degree of the curve). By way of further example, another curve fit methodology utilizes shape estimation as used in image recognition.

One advantageous methodology involves the processor accumulating the differences between the sampled temperatures and a starting temperature over the sampling period to generate a thermal response value. To that end, the thermal response ("TR") represented by curve 102 is determined by accumulating the differences between the sampled temperature $T_x$ at each interval $t_y$ and the initial temperature $T_i$ at $t_0$ until $t_n$ at which last temperature sample $T_x$ taken is considered as $T_z$. The thermal response is thus represented by the formula:

$$TR = \Sigma (T_x - T_i) \text{ (for } x = i \text{ to } z)$$

The various values of $T_x$, and at least $T_i$, may be stored in the memory 70 and the other values stored and/or used by the processor 60 on the fly to keep a running total for TR. Also, a base-line value ("BL") represented by curve 100 is determined based on the temperature samples $T_i$ and $T_z$ taken at or near the beginning and end of the activation period, respectively, according to the formula:

$$BL = (T_z - T_i) \times n/2$$

Armed with the values for TR and BL, the processor 60 can compare them to determine if they exceed a threshold corresponding to a pre-selected differential between curves 100 and 102 below which (or at or below which in some embodiments) the humidification chamber 20 is determined to be effectively dry. For example, in the embodiment shown here, the threshold is 1.1, such that the ratio of TR:BL is taken and compared against the value of 1.1. If the ratio exceeds the threshold, then the humidification chamber 20 is expected to have a high enough level of water 18 therein as not to be considered effectively dry. The processor 60 may make the determination that the humidification chamber 20 is not effectively dry, i.e., that there is an acceptable level of water 18 in the humidification chamber 20. If, however, the ratio does not exceed (i.e., is at or below) the threshold, then a determination is made that the humidification chamber 20 is effectively dry and appropriate action may be taken, such as initiating an alarm at the user interface 72 (or by sending an alarm signal over a network if heater unit 16 is equipped for such communication).

Figure 4:
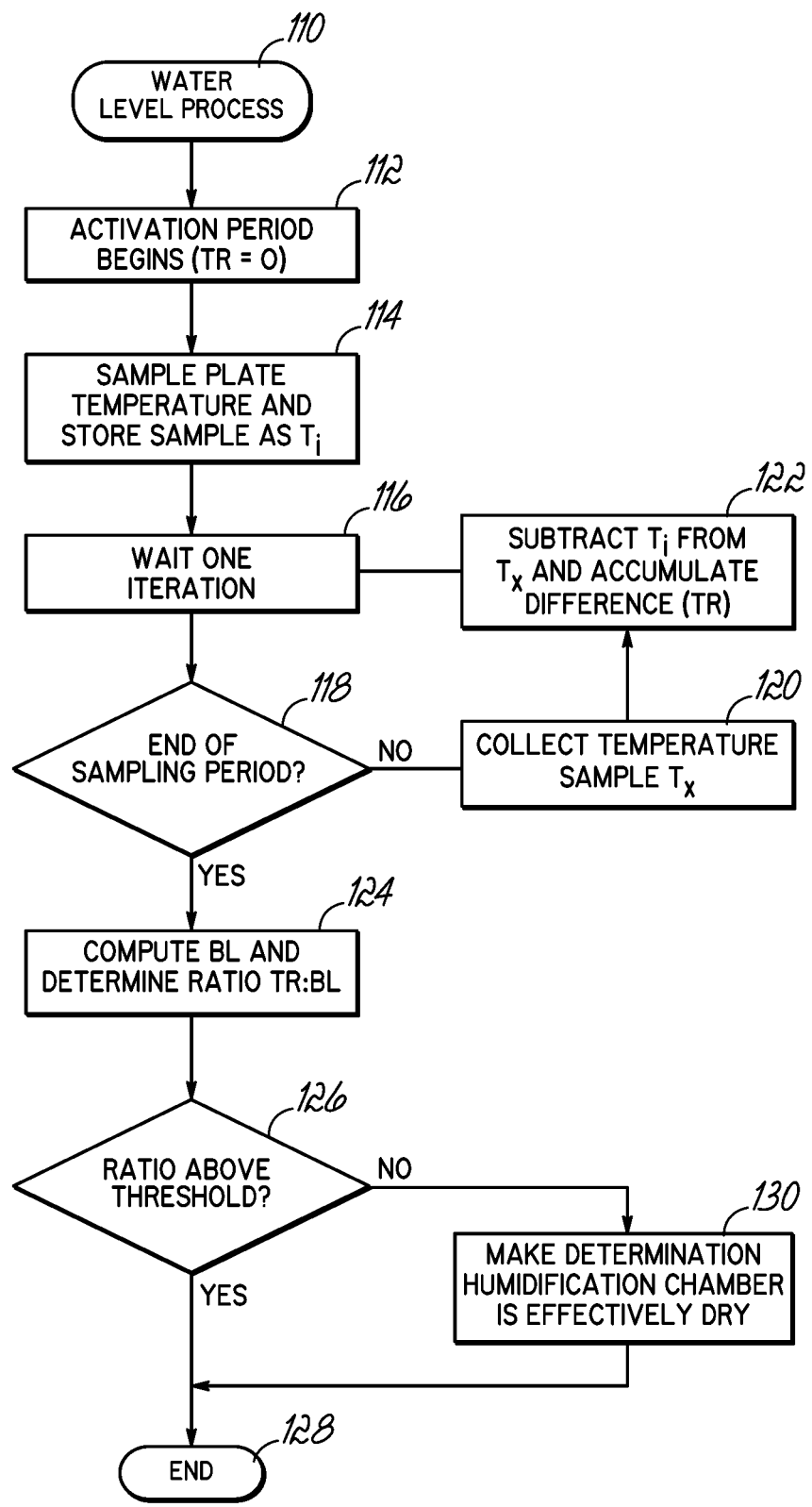
FIG. 4 is a flow chart of a process to detect whether the humidification chamber of the system of FIG. 1 is effectively dry based on the diagram of FIG. 3 in accordance with the principles of the first aspect of the present invention.

An exemplary method in accordance with the first aspect of the present invention will be described with further reference to FIG. 4. In particular, the respiratory system 10 is running and a water level process 110 is initiated at step 112, coincident with or shortly after the controller 50 initiates an activation period. At step 112, the thermal response value (TR) may be reset to zero. At step 114, the controller 50 obtains a sample of the plate temperature 44 from the temperature sensor 42 at or near $t_0$, and stores the sample in memory 70 as the initial temperature sample $T_i$. The sample $T_i$ might be taken in conjunction with time $t_0$, or might be the last sample taken before that time or the very first after that time, depending upon the timing of the samples by the processor 60. At step 116, the controller 60 waits for one iteration, such as one second, and then determines if the sampling period has ended at step 118. If not, then another plate temperature 44 is obtained at time $t_y$ as temperature sample $T_x$ at step 120, and the initial temperature sample value ($T_i$) is subtracted from the current temperature sample $T_x$ and the result accumulated as a running total for TR at step 122 with the process returning to step 116. Steps 116, 118, 120, and 122 may be repeated until the end of the sampling period is reached as determined at a step 118, in which case the process proceeds to step 124 to compute BL, and determine the ratio of TR:BL, such as by dividing TR by BL based on the last temperature sample $T_z$ obtained up to or at the end $t_n$ of the sampling period (or immediately thereafter in another embodiment).

The controller 50 then compares the ratio to a threshold at step 126. Where the ratio is greater than the threshold, that correlates to the area between the curve 102 and curve 100 being sufficiently large that it can be assumed that the humidification chamber 20 is not effectively dry. In that regard, the process goes on to step 128 whereat no determination is made that the humidification chamber 20 is effectively dry and instead the process ends to await the next activation period. Although not shown, a determination can be made at step 128 that the humidification chamber 20 has an acceptable level of water 18 therein. If at step 126 the ratio is not greater than the threshold (i.e., the ratio is less than or equal to the threshold), that is an indication that the curve 102 has moved sufficiently close to or has aligned with curve 100 such that the humidification chamber 20 can be considered to be effectively dry. Thus, at step 130, the controller 50 makes a determination that the humidification chamber 20 has effectively run dry and appropriate action may be taken (examples of which might be causing an audible and/or visual alarm at the user interface 72 so as to alert a caregiver (not shown) that the heater unit 16 requires attention), after which the process ends as at step 128 to await the next activation period.

Although shown as involving a sampling period during an activation period to determine whether the humidification chamber 20 is effectively dry during heating, the process described herein could be applied to a sampling period during a cooling period in accordance with the principles of this first aspect of the invention by evaluating the thermal response of the hot plate 32 as it cools down. In that regard, the thermal response has an arced behavior relative to a straight line defined between samples at respective ends of the sampling period during the cooling period which can be evaluated in generally the same manner as described above.

As will be appreciated, the foregoing utilizes a thermostatic type of control algorithm by which the heater element 40 is turned on or energized at the beginning of the activation period based on the gas temperature 48 falling to about the low temperature threshold and turned off at the end of the activation period based on the gas temperature rising to about the high temperature threshold, and with an activation period that is at least long enough to encompass the duration. In accordance with the principles of a second aspect of the invention, to reliably determine whether the humidification chamber 20 is effectively dry, it is desirable to maintain an activation period that is at or close to an optimum time period, such as eighty five seconds in the case of the hot plate 32 and the humidification chamber 20.

To seek to maintain that optimum activation period, controller 50 is adapted to vary the level of heating of hot plate 32 for an activation period by adjusting the power level to heater element 40 based on the duration of a prior activation period, such as the immediately preceding activation period. To that end, and in accordance with the principles of this second aspect of the present invention, the duration of any first (meaning first in time in relation to a later activation period and not necessarily the first in operation) activation period ($t_{d1}$) is determined, such as by subtracting the start time from the end time thereof. If the value of $t_{d1}$ obtained exceeds the optimum activation period, then in a subsequent activation period (referred to as a second activation period in that it occurs sometime after the end of the first activation period and might be after one or more intervening cooling periods of time and/or activation periods), the power level to heater element 40 is to be increased so as to attempt to shorten $t_{d1}$ in that subsequent activation period. Similarly, if the value of $t_{d1}$ obtained is less than the optimum activation period, then for a second activation period, the power level to heater element 40 is to be decreased so as to attempt to increase $t_{d1}$ in that second activation period. In either case, the processor 60 adjusts the power level to the heater element 40 by issuing a power signal 82 to PWM 66 which causes the duty cycle of closing of the power switch 68 to increase or decrease as appropriate. By way of example, where the power level is to be equal to some percentage of the maximum power level (such as where the switch is to be effectively closed at all times during an activation period), the power signal 82 may cause the switch to be effectively closed for that same percentage of each second during the activation period. Other duty cycles arrangements will be readily apparent to those skilled in the art.

The power signal 82 may advantageously be initially set to cause a predetermined power level to be supplied to the heater element 40, such as 75 watts. The power signal 82 may then be adjusted in proportion to the magnitude difference between $t_{d1}$ and the optimum activation period such that the larger the magnitude, the greater the increase or decrease in duty cycle. By way of example, the duty cycle may be changed sufficiently to increase or decrease the power level to the heater element 40 in proportion to the departure between the previous activation period and the optimum activation period. By way of further example, the new power signal 82 for a subsequent activation period ($PS_{New}$) may be calculated by the following formula:

$$PS_{New}=(PS_{OLD} \times (0.7+(0.3 \times D_{Prior})/D_{Opt})$$

where $PS_{OLD}$=the old power signal 82 for the prior activation period; $D_{Prior}$=the duration of the prior activation period; and $D_{Opt}$=the optimum activation period.

In some situations, the higher temperature threshold may not be attained until long after the desired optimum activation period, if at all. To that end, if the duration of the present (i.e., the first) activation period extends beyond some multiple of the optimum activation period ("extended period"), such as 2.0 times the optimum activation period, the processor 60 will automatically increment the power level to the heater element 40 by a fixed amount, such as 25 watts or, alternatively, by a multiple such as 1.2 times the current power level. A new, i.e., a second, activation period will be deemed to have been started with the new power level implemented in order to bring the duration of the activation period toward, and advantageously within range of, the optimum activation period. Also, a new sampling period may be started so as to again determine whether the humidification chamber 20 is effectively dry. If the activation period at this higher power level is within the extended period, then operation will continue as previously described. However, if the activation period is still not within the extended period, the processor 60 will again automatically increment the power level to the heater element 40 and the foregoing repeated until the maximum power level available is supplied to the heater element 40. If, at that maximum power level, the duration of the activation period still exceeds the extended period, then the heater element 40 will be turned off to allow the hot plate 32 to cool ("cool down period"). The cool down period may be for a fixed period of time or for a fixed drop in temperature or a combination thereof such as until the hot plate temperature drops by 8° C. or for twenty seconds, whichever first occurs. The heater element 40 is then turned on at full power (i.e., it is full-on) to start another, second activation period and for taking of temperature samples over a sampling period to again determine whether the humidification chamber 20 is effectively dry.

If the maximum power level is being used, another cool down period may be initiated at a time equal to the extended period if the activation period has not ended by then. In that case, thereafter using the same extended period to determine when to initiate a cool down period might lead to less than complete heating of the gas 23 passing through the humidification chamber 20. Such situations might occur, for example, if the air flow rate through the humidification chamber 20 is very high, although other situations might create that same condition. To that end, after a cool down period following an activation period during which the heater element 40 was powered full-on, the processor 60 will use an increased extended period, such as an extended period that has been extended by 5%. The processor 60 will continue to increase the extended period, such as by 5%, for a subsequent second activation period after a prior, first activation period which does not end before the currently increased extended period. The extended period may be increased up to a cap, such as 160 seconds. However, once the duration of an activation period falls below the optimum activation period, the power level will be decreased in order to increase a subsequent activation period as previously described.

With the foregoing, it is thus possible to adjust the duration of activation periods to be at or sufficiently close to an optimum activation period so as not to compromise the ability of the processor 60 to determine if the humidification chamber 20 is effectively dry. It will be appreciated, however, that depending upon the dynamics of the particular system involved, it may not be necessary to adjust the duration of an activation period or the sampling period in order to determine if the humidification chamber 20 is effectively dry. Similarly, the advantages of some or all features of this second aspect of the invention may be employed for reasons other than, and without regard to a system that involves, determination of whether the humidification chamber is effectively dry.

In addition to the foregoing, it may be helpful to know the air flow rate of the gas 23 through the humidification chamber 20, such as for control or notification purposes. In accordance with a third aspect of the present invention, we have made the surprising discovery that it is possible to approximate the actual, average air flow rate from the temperature of the hot plate 32, without the need for added sensors or complex computations. In that regard, it has been determined that for a given temperature set point, the average air flow rate can be empirically determined based on single temperature sample of the hot plate 32 taken at a relatively fixed point in the heating cycle having a predetermined relationship to the start of an activation period. Advantageously, the temperature sample is taken during the cooling period. By way of example, in the embodiment shown here, the temperature sample used is the last plate temperature sample taken during the cooling cycle just prior to the beginning of the next or second activation period (referred to for sake of reference as $T_c$). In an exemplary embodiment, we have determined that the air flow rate (A) can be approximated by multiplying the plate temperature 44 taken at the last sample ($T_c$) just before, or coincident with the start of the activation period by a constant related to the set point temperature ($a[T_{ch}]$), and offset by a second constant related to the set point temperature ($b[T_{ch}]$), as exemplified by the following formula:

$$A = a[T_{ch}] \times T_c + b[T_{ch}]$$

In an exemplary embodiment, for a temperature set point equal to the standard human body temperature (i.e., 98.6° F. or 37° C.), $a[T_{ch}]$ is determined to be 1.61 and $b[T_{ch}]$ is determined to be −73.52. Processor 60 may be adapted to compute the air flow rate using the above formula using the last sampled temperature from thermocouple 42 before the beginning of the activation period. Alternatively, to reduce the load on the processor 60, a look-up table (not shown) may be loaded into memory 70 containing air flow rate numbers for a range of temperature readings, and the last sampled temperature used as the look-up basis to obtain the air flow rate number from the look-up table.

As the standard human body temperature is typical for set points in respiratory systems, the foregoing will be sufficient to provide the air flow rate for system 10 which is described here as in the case of use with a human patient. Where other set points are to be used, the constants and/or the values in the look-up table may be different. On the other hand, it may be sufficient, irrespective of the set point, to use the above-described formula and/or look up table as it is considered typical that the set point for system 10 will not vary sufficiently from the standard human body temperature to induce more than an acceptable amount of error, say less than about 20%, between the actual air flow rate, and the estimated air flow rate using the principles explained above. In any event, there is thus provided a simple method by which the heater unit 16 may be adapted to estimate the air flow rate of the gas 23.

Once the air flow rate estimate is obtained, it may be used by processor 60 for a number of functions. By way of example, the air flow rate could be displayed on the user interface 72. The caregiver (not shown) may use that information as a check on the system 10. Alternatively, or additionally, a notification could be given to the caregiver, such as an alarm from the user interface 72, if the air flow rate suddenly changes from a prior estimate to a present estimate. The air flow rate could also be used by the controller 50 to facilitate management of the heater element 40 such as for adjusting the PID coefficients in a closed loop heating and humidification control system as exemplified by the aforementioned U.S. Patent Publication No. 2009/0110379. Alternatively or additionally, the air flow rate could be used to adjust one or more of the PID coefficients utilized by the processor 60 or another processor (not shown) to control the heater elements (not shown) which may be associated the inspiratory and/or expiratory limbs of the breathing circuit (also not shown), to adjust the power levels applied to heater elements, if present, in the breathing circuit such as to facilitate reduction in rain out therein.

In use, the humidification chamber 20 is mounted to the heater unit 16, and heater unit 16 operates to conduct heating cycles aimed at outputting heated and humidified breathable gas 11 at a desired gas temperature set point. The processor 60 of the controller 50 monitors the temperature of the hot plate 32 during an activation period of the heating cycle to determine if level of the water 18 in the humidification chamber 20 is considered acceptable or if, instead, there is either no water 18 left in the humidification chamber 20 or there is so little of the water 18 left in the humidification chamber 20 that effective humidification is not likely, as exemplified by the curve 102 having nearly or actually approached the curve 100. In those situations, the humidification chamber 20 is determined to be effectively dry by the processor 60. Further, the power level to the heater element 40 will be varied so as to attempt to maintain an activation period that is close to or at an optimum activation period. Also, the air flow rate of the gas 23 through the humidification chamber 20 is approximated by the processor 60. The foregoing is all accomplished using the thermocouple 42 and the probe 46 as are typically included with a heater unit 16 in operation, so as not to require additional sensors and the complications created thereby.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, temperature sample times and optimum activation period may be varied in alternative embodiments of the invention. The various temperature samples could also be averaged or otherwise processed to reduce noise or improve the accuracy of the determination of whether the humidification chamber 20 is effectively dry and/or the air flow rate. Measurements may also be used to update look-up table values or other system parameters so that the system adapts to conditions specific to its particular environment. Also, while ventilator 12 is shown as driving the gas 23 to and through humidification chamber 20, it will be appreciated that other gas systems could be employed, such as from a hospital oxygen supply, a CPAP or BiPAP pump, or other air or oxygen pumping system. Moreover, the various temperatures may be monitored and heater unit 16 shut down and/or an alarm set off if any of the temperature readings exceeds a maximum level, or if the differential between the set point temperature and the gas temperature becomes too great. Yet further, while humidification chamber 20 is shown as using water 18 as the liquid to humidify the gas 23, it will be appreciated that other liquids could be used depending upon the circumstances. In that same regard, while the heater unit 16 has been described in the context of the system 10 for use with breathable gas 11 in a respiratory system, the principles of the various aspects of the present invention may be individually and/or collectively applied to other heater units adapted to provide heat into a chamber of liquid for heating and humidifying a gas passed through the chamber. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. A heater unit to which a humidification chamber is to be thermally coupled, said humidification chamber adapted to hold liquid and to impart heat and humidity to a gas passing through said humidification chamber, the heater unit comprising:
    a hot plate thermally coupleable to said humidification chamber;
    a heater element thermally coupled to the hot plate;
    a temperature sensor thermally coupled to the hot plate providing plate temperature signals; and
    a processor receiving the plate temperature signals and determining therefrom a thermal response of the hot plate over a period of time, the processor further determining based on the thermal response of the hot plate if said humidification chamber thermally coupled to the plate is effectively dry.

2. The heater unit of claim 1, the processor determining if said humidification chamber is effectively dry by:
    determining a curve of the thermal response and determining whether the humidification chamber is effectively dry based on the degree of the curve.

3. The heater unit of claim 1, the processor determining if said humidification chamber is effectively dry by:
    determining the thermal response of the hot plate by accumulating the difference in the plate temperature signals at a plurality of samples over the period of time relative to a first plate temperature signal at or near the beginning of the period of time;
    determining a base-line value by correlating the difference between the plate temperature signals at or near the beginning and the end of the period of time; and
    comparing the thermal response to the base-line value.

4. The heater unit of claim 3, the processor determining if said humidification chamber is effectively dry if the comparison between the thermal response and the base-line value does not exceed a threshold value.

5. The heater unit of claim 3, the processor not determining if said humidification chamber is effectively dry if the comparison between the thermal response and the base-line value exceeds a threshold value.

6. The heater unit of claim 1 wherein the period of time defines a sample period within an activation period during which the heater element is energized.

7. The heater unit of claim 6, the processor further selectively energizing the heater to begin an activation period when the temperature of conditioned gas from said humidification chamber decreases to about a low temperature threshold and selectively de-energizing the heater element to end the activation period when the temperature of the conditioned gas increases to about a high temperature threshold, the thresholds correlated to a gas temperature set point.

8. The heater unit of claim 7, the processor determining a duration of a first activation period and, if the duration departs from an optimum activation period, adjusting the energization level of the heater element for a subsequent activation period in relation to the duration whereby to change a duration of the subsequent activation period toward the optimum activation period.

9. The heater unit of claim 8, the processor increasing the energization level if the duration of the first activation period exceeds the optimum activation period and decreasing the energization level if the duration of the first activation period is less than the optimum activation period.

10. The heater unit of claim 8, the processor adjusting the energization level proportional to the difference between the duration of the first activation period and the optimum activation period.

11. The heater unit of claim 7, the processor increasing an energization level of the heater element if the activation period exceeds a multiple of an optimum activation period.

12. The heater unit of claim 7, the processor further selectively de-energizing the heater element during a cooling period subsequent to a first activation period during which the gas temperature of conditioned gas from said humidification chamber decreases toward the low temperature threshold and selectively re-energizing the heater element for a second activation period, processor further determining an air flow rate of gas through said humidification chamber based on one of the plate temperature signals received in predetermined relationship to the beginning of the second activation period.

13. The heater unit of claim 1 in combination with a humidification chamber, the humidification chamber having a plastic dome-shaped body and a bottom plate, the bottom plate being in thermal communication with the hot plate, the humidification chamber adapted to hold liquid and to impart heat and humidity to a gas passing therethrough.

14. A heater unit to which a humidification chamber is to be thermally coupled, said humidification chamber adapted to hold liquid and to impart heat and humidity to a gas passing through said humidification chamber, the heater unit comprising:
a hot plate thermally coupleable to said humidification chamber;
a heater element thermally coupled to the hot plate; and
a processor selectively energizing the heater element to begin an activation period when the temperature of conditioned gas from said humidification chamber decreases to about a low temperature threshold and de-energizing the heater element to end an activation period when the temperature of conditioned gas from said humidification chamber increases to about a high temperature threshold, the thresholds correlated to a gas temperature set point, the processor determining a duration of a first activation period and, if the duration departs from an optimum activation period, adjusting the energization level of the heater element for a subsequent activation period in relation to the duration whereby to change a duration of the subsequent activation period toward the optimum activation period.

15. The heater unit of claim 14, the processor increasing the energization level if the duration of the first activation period exceeds the optimum activation period and decreasing the energization level if the duration of the first activation period is less than the optimum activation period.

16. The heater unit of claim 14, the processor adjusting the energization level proportional to the difference between the duration of the first activation period and the optimum activation period.

17. The heater unit of claim 14, the processor increasing energization level of the heater element if the activation period exceeds a multiple of the optimum activation period.

18. The heater unit of claim 14 further comprising a temperature sensor thermally coupled to the hot plate providing plate temperature signals, the processor receiving the plate temperature signals and determining an air flow rate of gas through said humidification chamber based on one of the plate temperature signals received in predetermined relationship to the beginning of an activation period.

19. The heater unit of claim 14 in combination with a humidification chamber, the humidification chamber having a plastic dome-shaped body and a bottom plate, the bottom plate being in thermal communication with the hot plate, the humidification chamber adapted to hold liquid and to impart heat and humidity to a gas passing therethrough.

20. A heater unit to which a humidification chamber is to be thermally coupled, said humidification chamber adapted to hold liquid and to impart heat and humidity to a gas passing through said humidification chamber, the heater unit comprising:
a hot plate thermally coupleable to said humidification chamber;
a heater element thermally coupled to the hot plate;
a temperature sensor thermally coupled to the hot plate providing plate temperature signals; and
a processor receiving the plate temperature signals and selectively energizing the heater element when the temperature of conditioned gas from said humidification chamber decreases to a low temperature threshold to begin an activation period and selectively de-energizing the heater element when the temperature of conditioned gas from said humidification chamber increases to about a high temperature threshold to begin a cooling period, the thresholds correlated to a gas temperature set point, the processor further determining an air flow rate of gas through said humidification chamber based on one of the plate temperature signals received in predetermined relationship to the beginning of an activation period.

21. The heater unit of claim 20, the processor determining an air flow rate of gas through said humidification chamber based on one of the plate temperature signals received in the cooling period.

22. The heater unit of claim 21, the processor determining an air flow rate of gas through said humidification chamber based on the plate temperature signal last received during the cooling period before the beginning of a subsequent activation period.

23. A method of determining if a humidification chamber thermally coupled to a hot plate of a heater unit is effectively dry, the humidification chamber adapted to impart heat and humidity to a gas passing therethrough, the method comprising:
applying heat to the hot plate for a first activation period to increase gas temperature of the gas to which heat and humidity are being imparted;
determining a thermal response of the hot plate from temperature samples taken of the hot plate for a period of time during the first activation period; and
determining, based on the thermal response, if the humidification chamber is effectively dry.

24. The method of claim 23 further comprising determining a curve of the thermal response and determining whether the humidification chamber is effectively dry based on the degree of the curve.

25. The method of claim 23, wherein determining the thermal response includes accumulating the difference in a plurality of the temperature samples over the period of time relative to a first temperature sample at or near the beginning of the period of time, the method further comprising determining a base-line value by correlating the difference between temperature samples taken at or near the beginning and the end of the period of time, and wherein determining if the humidification chamber is effectively dry includes comparing the thermal response to the base-line value.

26. The method of claim 25, wherein the determination that the chamber is effectively dry is made if the comparison between the thermal response and the base-line value does not exceed a threshold value.

27. The method of claim 25, wherein the determination that the chamber is effectively dry is made if the comparison between the thermal response and the base-line value is below a threshold value.

28. The method of claim 23 further comprising monitoring the gas temperature and starting the first activation period when the gas temperature decreases to about a low temperature threshold and ending the first activation period when the gas temperature increases to about a high temperature threshold.

29. The method of claim 28, the period of time starting after the first activation period starts and ending before the first activation period ends.

30. The method of claim 28, wherein applying heat includes applying a power level to a heater element thermally coupled to the hot plate for the first activation period, the method further comprising applying heat to the hot plate for a second, subsequent activation period after the gas temperature has again decreased to about the low temperature threshold, determining a duration of the first activation period, and if the duration of the first activation period departs from an optimum period adjusting the power level to the heater element for the second activation period in relation to the duration whereby to change a duration of the second activation period toward the optimum period.

31. The method of claim 30, the power level applied to the heater element for the second activation period being increased if the duration of the first activation period exceeds the optimum period and being decreased if the duration of the first activation period is less than the optimum period.

32. The method of claim 30, the power level applied to the heater element for the second activation period being adjusted proportional to the difference between the duration of the first activation period and the optimum period.

33. The method of claim 28, the method further comprising increasing an energization level of a heater element thermally coupled to the hot plate if the duration of the first activation period exceeds a multiple of an optimum period.

34. The method of claim 23 further comprising not applying heat to the hot plate for a cooling period after the first activation period to decrease gas temperature toward a low temperature threshold, re-applying heat to the hot plate for a second activation period, and determining an air flow rate of the gas based on a temperature of the hot plate in predetermined relationship to the beginning of the second activation period.

35. A method of controlling a period of heating of a humidification chamber thermally coupled to a hot plate of a heater unit, the humidification chamber adapted to impart heat and humidity to a gas passing therethrough, the method comprising:

applying heat to the hot plate for a first activation period to increase gas temperature of the gas to which heat and humidity are being imparted, the heat being applied by applying a power level to a heater element thermally coupled to the hot plate;

applying heat to the hot plate for a subsequent, second activation period;

determining a duration of the first activation period, and if the duration of the first activation period departs from an optimum period adjusting the power level to the heater element for the second activation period in relation to the duration of the first activation period whereby to change a duration of the second activation period toward the optimum period.

36. The method of claim 35 further comprising increasing the power level for the second activation period if the duration of the first activation period exceeds the optimum period and decreasing the power level for the second activation period if the duration of the first activation period is less than the optimum period.

37. The method of claim 36 further comprising adjusting the power level for the second activation period proportional to the difference between the duration of the first activation period and the optimum period.

38. The method of claim 36 further comprising increasing the power level if the duration of the first activation period exceeds a multiple of the optimum period.

39. The method of claim 36 further comprising determining an air flow rate of the gas based on a temperature sample taken of the hot plate in predetermined relationship to the beginning of the second activation period.

40. The method of claim 39 further comprising allowing the gas temperature to decrease during a cooling period between the first and second activation periods and determining an air flow rate of the gas based on a temperature sample taken of the hot plate during the cooling period in predetermined relationship to the beginning of the second activation period.

41. A method of determining air flow rate of a gas passing through a humidification chamber thermally coupled to a hot plate of a heater unit, the humidification chamber adapted to impart heat and humidity to the gas passing therethrough, the method comprising:

applying heat to the hot plate for a first activation period to increase gas temperature of the gas to which heat and humidity are being imparted;

applying heat to the hot plate for a second activation period;

obtaining a temperature sample of the hot plate in predetermined relationship to the beginning of the second activation period; and determining an air flow rate of the gas based on the temperature sample.

42. The method of claim 41 further comprising allowing the gas temperature to cool during a cooling period between the first and second activation periods, and wherein the temperature sample is obtained during the cooling period.

43. The method of claim 42, wherein the temperature sample is obtained as the last sample before the second activation period.

* * * * *